United States Patent [19]

Quay

[11] Patent Number: 5,087,439

[45] Date of Patent: * Feb. 11, 1992

[54] PARAMAGNETIC METAL-DIETHYLENETRIAMINE-PENTAACETIC ACID PARTIAL AMIDE COMPLEXES FOR MAGNETIC RESONANCE IMAGING

[75] Inventor: Steven C. Quay, Palo Alto, Calif.

[73] Assignee: Salutar, Inc., Sunnyvale, Calif.

[ * ] Notice: The portion of the term of this patent subsequent to Aug. 18, 2004 has been disclaimed.

[21] Appl. No.: 386,806

[22] Filed: Jul. 31, 1989

Related U.S. Application Data

[63] Continuation-in-part of Ser. No. 855,223, Apr. 24, 1986, Pat. No. 4,859,451, which is a continuation-in-part of Ser. No. 657,676, Oct. 4, 1984, Pat. No. 4,687,658, and a continuation-in-part of Ser. No. 671,106, Nov. 13, 1984, Pat. No. 4,687,659.

[51] Int. Cl.$^5$ .............. G01N 24/00; G01N 31/00; C07F 13/00; C07F 11/00
[52] U.S. Cl. .......................... 424/9; 436/173; 436/806; 556/45; 556/57; 556/110; 556/138; 556/148
[58] Field of Search ............ 424/9; 556/148, 45, 556/57, 110, 138; 436/173, 806; 128/654, 635 CA

[56] References Cited

U.S. PATENT DOCUMENTS 4,352,751 10/1982 Wieder et al. ................ 530/303
4,647,447 3/1987 Gries et al. .................... 424/9

FOREIGN PATENT DOCUMENTS 49-022422 2/1974 Japan .

OTHER PUBLICATIONS

Minagawa et al., Chem. Abs. 81(16):92489q, (1974).
Grana-Molares et al., Analusis 7(5):249-252, (1979).
Grana-Molares et al., Acta Quim. Compostelana 2(4):127-134, (1978).
Svedaite, T. et al., Liet. TSR Mokslu Akad. Darb. Ser B(4), pp. 59-63, (1983).
Bulman, Ra et al., Naturwlssenschaften 68(9):483-485, (1981).

*Primary Examiner*—Glennon H. Hollrah
*Assistant Examiner*—Gary E. Hollinden
*Attorney, Agent, or Firm*—Cushman, Darby & Cushman

[57] ABSTRACT

Complexes of a highly paramagnetic polyvalent metal, e.g., a lanthanide such as gadolinium, or of a less paramagnetic metal, e.g., iron, manganese, copper, cobalt, chromium or nickel, with a bisalkylamide of diethylenetriaminepentaacetic acid of the formula:

$$\begin{array}{c}
\text{M}-\overset{\overset{\displaystyle O}{\|}}{\text{C}}-\text{H}_2\text{C} \\
\text{M}-\underset{\underset{\displaystyle O}{\|}}{\text{C}}-\text{H}_2\text{C}
\end{array}
\text{N}-\text{CH}_2\text{CH}_2-\text{N}-\text{CH}_2\text{CH}_2\text{N}
\begin{array}{c}
\text{CH}_2-\overset{\overset{\displaystyle O}{\|}}{\text{C}}-\text{M} \\
\text{CH}_2-\underset{\underset{\displaystyle O}{\|}}{\text{C}}-\text{M}
\end{array}
$$
$$\text{CH}_2-\overset{\overset{\displaystyle O}{\|}}{\text{C}}-\text{M}$$

wherein three groups M are hydroxyl groups and the remaining two groups M are NHR groups in which each group R is an alkyl group of the formula $-(\text{CH}_2)_n\text{CH}_3$ where n is zero or an integer of from 1 to 17, are disclosed. These complexes are useful as magnetic resonance imaging contrast enhancers.

21 Claims, No Drawings

PARAMAGNETIC METAL-DIETHYLENETRIAMINE-PENTAACETIC ACID PARTIAL AMIDE COMPLEXES FOR MAGNETIC RESONANCE IMAGING

CROSS REFERENCE TO RELATED APPLICATIONS

This is a continuation-in-part of copending patent application Ser. No. 855,223 filed Apr. 24, 1986 now U.S. Pat. No. 4,859,451 which is itself a continuation-in-part of patent application Ser. No. 657,676, filed Oct. 4, 1984, now U.S. Pat. No. 4,687,658, issued Aug. 18, 1987, and Ser. No. 671,106, filed Nov. 13, 1984, now U.S. Pat. No. 4,687,659, also issued Aug. 18, 1987. The contents of these patents and patent applications are incorporated herein by reference in their entirety.

BACKGROUND OF THE INVENTION

The present invention relates to improvements in the enhancing of nuclear magnetic resonance (NMR) imaging of a subject, e.g. organs of a patient.

X-rays have long been used to produce images of internal organs of a patient, the patient being positioned between a source of x-rays and a film sensitive to the rays. Where organs interfere with the passage, the film is less exposed and the resulting picture, upon development of the film, is an indication of the state of the organ.

More recently, another imaging technique has been developed, viz. nuclear magnetic resonance imaging. This avoids the harmful effects sometimes attending X-ray exposure. For improved imaging with x-rays, patients have been given enhancers prior to imaging, either orally or parenterally. After a predetermined time interval for distribution of the enhancer through the patient, the image has been taken. The time of good imaging is desirably as short as possible after taking the enhancer; on the other hand there is a decay in the effectiveness, so desirably the decay is relatively slow so as to provide a substantial time interval during which imaging can be done. The present invention relates to enhancers in NMR imaging.

Australian patent application 86 330/82 of July 22, 1982 and U.S. Pat. No. 4,647,447 (Gries, et al.), issued Mar. 3, 1987, disclose the use as an NMR image enhancer of a complex salt, preferably the gadolinium chelate of diethylenetriaminetetraacetic acid, plus an amine. From the data reported therein these appear to perform well. However, this compound is highly ionic and is rapidly excreted by the kidneys, making the timing of the injection extremely critical. Furthermore, there is virtually no uptake by any solid organ, such as the heart, pancreas or liver. Moreover, an amine is also required.

SUMMARY OF THE INVENTION

It is accordingly an object of the present invention to provide alternative image enhancers which avoid one or more of the aforementioned disadvantages. It is another object of the invention to reduce the total number of particles from three to one, thereby decreasing the osmolarity and improving the safety without affecting the efficacy of the enhancer compound.

It is still another object of the invention to provide a compound which may be used for enhancing NMR images of the heart or liver.

These and other objects and advantages are realized in accordance with the present invention pursuant to which the image enhancer comprises a complex of a paramagnetic metal and a partial amide of diethylenetriaminepentaacetic acid of formula I

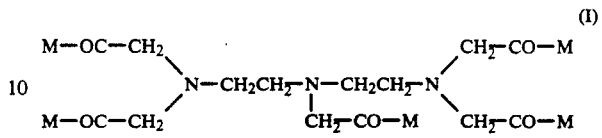

(in which three groups M are hydroxyl groups and the remaining two groups M are NHR groups where each group R is an alkyl group of formula $(CH_2)_nCH_3$ where n is 0 or an integer of from 1 to 17).

DETAILED DESCRIPTION OF THE INVENTION

While lanthanides and particularly gadolinium are highly paramagnetic and useful in accordance with the invention, it is surprising that other less paramagnetic metals perform well, e.g., iron, manganese, copper, cobalt, chromium and nickel.

The DTPA-bisalkylamide chelating agent of formula I can be produced by amidating the pentaacetic acid, which is commercially available, in a conventional manner with an amine. Thus, the pentaacetic acid may be reacted with two moles of a primary amine to produce the diamide.

Alternatively, the starting material instead of the pentaacetic acid can be the dianhydride thereof, also commercially available, and this too can be amidated.

Thus a general anhydride diamide method is suitable for making each homologue of the DTPA-bisalkylamide family of chelating agents of formula I. In the example below the paramagnetic metal is provided by $FeCl_3$. However other paramagnetic ions in other forms may be employed.

Step 1) Formation of DTPA-bisalkylamide

Mix DTPA-bisanhydride (diethylenetriaminepentaacetic acid anhydride; Sigma Chemical Co., St. Louis, Mo.) with an alkylamine $RNH_2$ in water (for lower alkylamines) or chloroform (for higher alkylamines). The ratio of amine to DTPA-bisanhydride is not critical as long as an excess of amine is provided.

Step 2)

Heat the solution for several hours, e.g. overnight, at reflux temperature to produce the bisalkylamide and water.

Step 3)

Remove the excess solvent by vacuum rotary evaporation to leave a DTPA-bisalkylamide crystal residue.

Step 4)

Mix the DTPA-bisalkylamide residue into an aqueous solution of $FeCl_3$, in stoichiometric proportions to form FeDTPA-bisalkylamide and HCl.

Step 5)

Remove the MCl (a) by evaporation using a rotary evaporator, (b) by neutralization using NaOH or $NH_4OH$, or (c) by chromatography using a silica gel column.

Step 6)

Remove water by vacuum-freezing to form a highly stable paramagnetic metal DTPA-bisalkylamide complex.

Step 7)

Disperse the complex in a suitable vehicle to provide a pharmacological form.

The DTPA-bisalkylamide chelating agents of formula I include homodiamides (where the groups R are identical), e.g.

| | |
|---|---|
| DTPA-bis methylamide | (R = CH$_3$) |
| DTPA-bis ethylamide | (R = C$_2$H$_5$) |
| DTPA-bis propylamide | (R = C$_3$H$_7$) |
| DTPA-bis butylamide | (R = C$_4$H$_9$) |
| DTPA-bis pentylamide | (R = C$_5$H$_{11}$) |
| DTPA-bis hexylamide | (R = C$_6$H$_{13}$) |
| DTPA-bis heptylamide | (R = C$_7$H$_{15}$) |
| DTPA-bis octylamide | (R = C$_8$H$_{17}$) |
| DTPA-bis nonylamide | (R = C$_9$H$_{19}$) |
| DTPA-bis decylamide to | (R = C$_{10}$H$_{21}$) |
| DTPA-bis hexadecylamide | (R = C$_{16}$H$_{33}$) |

Using more systematic nomenclature, these DTPA-bisalkylamides listed above may be named as 6-carboxymethyl-3,9-bis(methylcarbamoylmethyl)-3,6,9-triazaundecanedioic acid, 6-carboxymethyl-3,9-bis(ethylcarbamoylmethyl)-3,6,9-triazaundecanedioic acid, 6-carboxymethyl-3,9-bis(propylcarbamoylmethyl)-3,6,9-triazaundecanedioic acid, 6-carboxymethyl-3,9-bis(butylcarbamoylmethyl)-3,6,9-triazaundecanadioic acid, 6-carboxymethyl-3,9-bis(pentylcarbamoylmethyl)-3,6,9-triazaundecanadioic acid, 6-carboxymethyl-3,9-bis(hexylcarbamoylmethyl)-3,6,9-triazaundacanedioic acid, 6-carboxymethyl-3,9-bis(heptylcarbamoylmethyl)-3,6,9-triazaundecanadioic acid, 6-carboxymethyl-3,9-bis(octylcarbamoylmethyl)-3,6,9-triazaundecanadioic acid, 6-carboxymethyl-3,9-bis(nonylcarbamoylmethyl)-3,6,9-triazaundecanedioic acid, 6-carboxymethyl-3,9-bis(decylcarbamoylmethyl)-3,6,9-triazaundecanedioic acid, and 6-carboxymethyl-3,9-bis(hexadecylcarbamoylmethyl)-3,6,9-triazaundecanedioic acid.

The complex of the invention can be prepared by dissolving the amide in water or other solvent and adding a salt of the desired metal, e.g. ferric chloride. The solution can then be dialyzed or ion exchanged to remove chloride ions or an alkali such as NaOH can be added to neutralize the chloride ions, the by-product NaCl being removed or left in solution since it is physiologically acceptable.

Where the complexing metal is of a higher valence state than the complexing agent can accept, e.g. M(+4) the fourth M valence may be tied up as the chloride. When the metal is only divalent, for example Cu(+2), the extra site of the complexing agent may be neutralized as the sodium salt.

When the amide chain length increases, the complexes become increasingly oleophilic and chains of 12 or more carbon atoms slow down the movement to the kidneys due to temporary entrapment or enrichment in organs which have efficient fatty acid uptake systems such as the hepatobiliary system. Thus, such complexes are especially useful for liver imaging. Other organs such as the kidney, ureter, bladder, brain and heart can be imaged well with the lower homologues. Since the complexes do not penetrate the blood-brain-barrier under normal circumstances, they are useful in detecting the extravasation of arterial blood in the extravascular space during cerebral hemorrhaging and in the edema fluid surrounding tumors.

As noted, iron is the preferred metal, but other polyvalent paramagnetic metals may be used, e.g. manganese, chromium, cobalt, nickel, copper, and the like. The preferred lanthanide is gadolinium, but others such as lanthanum, cerium, praseodymium, neodymium, promethium, samarium, europium, terbium, dysprosium, holmium, erbium, thulium, ytterbium and lutetium may also be used.

The images can be taken in conventional manner using any of the machines currently available, e.g. that of Siemens AG of Erlanger, Federal Republic of Germany.

Further details of imaging systems are described in the prior art, e.g. "NMR, A Primer for Medical Imaging" by Wolf and Popp, Slack Book Division (ISBN 0-943432-19-7) and *Scientific American*, May 1982, pages 78-88.

The solution of the complex may be sterilized and made up into ampules or may be lyophilized into a powder for dissolution when ready to be used. The solution may be mixed with conventional additives such as saline solution, albumin, buffers and the like. If desired, ampules may be made up containing lyophilized powder of the complex in one compartment and a solution of additives in another separated from the first by a frangible barrier. When ready to use, the barrier is broken and the ampule shaken to form a solution suitable for use.

Immediately prior to actual administration of the contrast agent, the reconstituted solution is further diluted by addition of at least 100 ml (up to 1000 ml) of a suitable diluent such as:

Roger's Injection, USP
Sodium Chloride Injection, USP
Dextrose Injection, USP
  (5 percent Dextrose in sterile water)
Dextrose Sodium Chloride Injection, USP
  (5 percent Dextrose in Sodium Chloride)
Lactated Ringer's Injection, USP
Protein Hydrolysate Injection
  Low sodium, USP 5 percent
  5 percent with Dextrose 5 percent
  5 percent with Invert Sugar 10 percent
Roger's Injection, USP
Roger's Injection, USP The manner and dosage of administration and the manner of scanning are substantially the same as in the prior art. With solutions containing about 50 to 500 mmoles of the complex/liter, sufficient solution should be administered orally or parenterally to provide about 1 to 100 μmols/kg, corresponding to about 1 to 50 mol for an adult human patient.

For smaller patients or other animals, the dosage should be varied accordingly. The particular complex and organ to be imaged will determine the waiting period between administration and imaging. For kidney imaging, the cortical-medulla enhancement phase occurs 15–45 seconds after injection. For the heart and liver, the uptake occurs between 2 and 10 minutes after injection.

The invention will be further described in the following illustrative examples wherein all parts are by weight unless otherwise expressed.

EXAMPLES

EXAMPLE 1

Synthesis of DTPA Bis-alkylamide Derivatives (1) 5 g (14 mmol) of diethylenetriaminepentaacetic acid anhydride (Sigma Chemical Company) is placed in a round bottomed flask and 60 ml of chloroform are added. The mixture is stirred vigorously with a magnetic stirrer until all clumps of the anhydride are dispersed.

(2) A 4-fold molar excess of hexylamine (Aldrich Chemical Co.) (56 mmol) is gradually added to the stirring mixture.

(3) The reaction is allowed to continue for an additional hour with constant stirring. At this point, the reaction mixture is light yellow and clear.

(4) The chloroform and excess hexylamine is removed with a rotary evaporator and the resulting solids are washed twice in 95% ethanol and dried in a vacuum at room temperature overnight.

The formula weight of the compound (6-carboxymethyl-3,9-bis(hexylcarbamoylmethyl)-3,6,9-triazaundecanedioic acid (or DTPA-bishexylamide) is 860.71 and its structure is

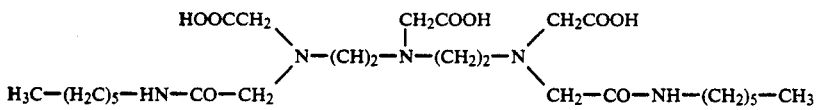

A gadolinium chelate of the compound was made in the following way:

(1) 28.04 (0.05 mol) of the DTPA-bisalkylamide compound was dissolved in 400 ml water.

(2) The pH of the dissolved material was adjusted to 4 and 18.59 g (0.05 mol) of gadolinium chloride hexahydrate (99.999%, Aldrich Chemical Co.) was added to the stirring mixture.

(3) The resulting drop in pH was gradually adjusted to 6.5 with a 5 N solution of sodium hydroxide.

(4) The volume of the solution was brought to 500 ml with distilled water. The clear, pale yellow solution was filtered through a 0.2 $\mu$m filter and stored in 30 ml vials sealed with a butyl rubber stopper.

Relaxivity of the compound in water and in human plasma at 10 MHz (37° C.) (for practical purposes, the lower the $T_1$ in a given part of the body, the brighter the image in MR imaging):

| Conc M | $T_1^*$ Plasma | $T_2^*$ Plasma | $T_1^*$ Water | $T_2^*$ Water |
|---|---|---|---|---|
| Gd DTPA-bishexylamide (inventive compound) | | | | |
| $9.34 \times 10^{-3}$ | 15 | 10 | 23 | 18 |
| $4.67 \times 10^{-3}$ | 26 | 21 | 42 | 36 |
| $2.34 \times 10^{-3}$ | 48 | 39 | 81 | 76 |
| $1.17 \times 10^{-3}$ | 83 | 71 | 159 | 147 |
| $5.84 \times 10^{-4}$ | 145 | 123 | 309 | |
| $2.92 \times 10^{-4}$ | 249 | | 561 | |
| $1.46 \times 10^{-4}$ | 403 | | 947 | |
| $7.30 \times 10^{-5}$ | 622 | | 1374 | |
| $3.68 \times 10^{-5}$ | 881 | | | |
| $1.82 \times 10^{-5}$ | 1087 | | | |
| $9.12 \times 10^{-6}$ | 1220 | | | |
| Gd DTPA-di(N-methylglucamine) (prior art product) | | | | |
| $6.25 \times 10^{-3}$ | 39 | 31 | 40 | 35 |
| $3.13 \times 10^{-3}$ | 69 | 61 | 83 | 76 |
| $1.56 \times 10^{-3}$ | 134 | 116 | 163 | 155 |
| $7.81 \times 10^{-4}$ | 240 | | 309 | |
| $3.91 \times 10^{-4}$ | 405 | | 582 | |
| $1.95 \times 10^{-4}$ | 636 | | 1015 | |
| $9.77 \times 10^{-5}$ | 877 | | | |

*$T_1$ and $T_2$ are relaxtion times in msec.

It is surprising that the Gd DTPA-bishexylamide is almost three times better at proton relaxation in plasma than the prior art compound Gd DTPA-di(N-methylglucamine).

Without wishing to be bound by any particular theory of operability, this enhanced relaxivity is probably due to protein binding in plasma by the oleophilic compounds. Koenig and Brown (D. H. Koenig and R. D. Brown, *Magnetic Resonance in Medicine* 1, 78–495 (1984)) teach that changes in rotational correlation times which should accompany the protein binding of small paramagnetic molecules, can give a substantial improvement in proton relaxivity. This can potentially allow lower doses in humans and thus provide a safer product.

EXAMPLE 2

Pharmacokinetics of the compound in a pure breed beagle dog

A male dog was injected with the test compounds at 100 $\mu$ mol/kg. Blood was drawn at the indicated times. The plasma was separated and the relaxivity measured.

| Time min. | $T_1$ (msec) Gd DTPA-bis-hexylamide (inventive compound) | $T_1$ (msec) Gd DTPA-di(N-methylglucamine) (prior art compound) |
|---|---|---|
| pre-inj | 1517 | 1427 |
| 10 | | 440 |
| 20 | 275 | 444 |
| 30 | 362 | 551 |
| 45 | 447 | 580 |
| 60 | 688 | 687 |
| 90 | 965 | 860 |
| 180 | 1340 | 1282 |
| 360 | 1610 | |

Again, it was surprising that, at the same dosage the compound according to the invention produced a blood $T_1$ value (275 msec) at 20 minutes which was substantially lower than that for the prior art compound (444 msec). This will produce a two-fold improvement in image signal intensity.

EXAMPLE 3

Organ distribution of the compound in male rabbits

The test compounds were injected into male rabbits at 100 $\mu$mol/kg. The rabbits were sacrificed at 15 minutes post injection and the relaxivity of internal organs was measured in vitro at 5 MHz.

| Time min. | $T_1$ (msec) Gd DTPA-bis-hexylamide (inventive compound) | $T_1$ (msec) Gd DTPA-di(N-methylglucamine) (prior art compound) |
|---|---|---|
| pre-inj | 1517 | 1427 |
| 10 | | 440 |
| 20 | 275 | 444 |
| 30 | 362 | 551 |
| 45 | 447 | 580 |
| 60 | 688 | 687 |
| 90 | 965 | 860 |
| 180 | 1340 | 1282 |

-continued

| Time min. | $T_1$ (msec) Gd DTPA-bis-hexylamide (inventive compound) | $T_1$ (msec) Gd DTPA-di(N-methyl-glucamine) (prior art compound) |
|---|---|---|
| 360 | 1610 | |

Again, it was surprising that, at the same dosage the compound according to the invention produced a blood $T_1$ value (375 msec) at 20 minutes which was substantially lower than that for the prior art compound (444 msec). This will produce a two-fold improvement in image signal intensity.

EXAMPLE 3

Organ distribution of the compound in male rabbits

The test compounds were injected into male rabbits at 100 μ mol/kg. The rabbits were sacrificed at 15 minutes post injection and the relaxivity of internal organs was measured in vitro at 5 MHz.

| Organs | $T_1$ (msec) Gd DTPA-bis-hexylamide (inventive compound) | $T_1$ (msec) Gd DTPA-di(N-methyl-glucamine) (prior art compound) | $T_1$ (msec) Normal Organs |
|---|---|---|---|
| Heart | 374 | 487 | 482 |
| Lung | 507 | 565 | 585 |
| Fat | 167 | 173 | 180 |
| Skeletal Muscle | 397 | 405 | 411 |
| Renal Costar | 179 | 242 | 342 |
| Renal Medulla | 218 | 379 | 782 |
| Liver | 176 | 251 | 260 |
| Spleen | 362 | 463 | 473 |
| Pancreas | 256 | 253 | 265 |
| Bladder | 308 | 272 | 511 |
| Stomach | 332 | 312 | 305 |
| Small intestine | 248 | 298 | 317 |
| Large intestine | 183 | 317 | 328 |

It is noted that the prior art compound fails to produce any change in spin lattice ($T_1$) relaxation in the heart and liver and thus would produce no noticeable image enhancement in these organs. The present invention is very effective in lowering $T_1$ in the liver and heart and thus produces image signal enhancement in these organs.

It will be understood that the specification and examples are illustrative but not limitative of the present invention and that other embodiments within the spirit and scope of the invention will suggest themselves to those skilled in the art.

What is claimed is:

1. In a process of NMR imaging of a subject comprising administering to said subject a composition containing an image-modifying effective amount of an image enhancer, permitting the enhancer to move through the subject, and after a time interval taking an NMR image of the subject, the improvement which comprises administering as said enhancer a complex of a paramagnetic polyvalent metal and a partial amide of diethylenetriaminepentaacetic acid of formula I

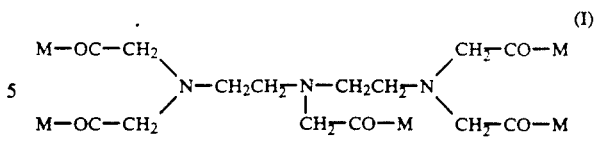

in which three groups M are hydroxyl groups and the remaining two groups M are NHR groups, where each group R is an alkyl group of formula —$(CH_2)_n CH_3$ where n is zero or an integer of from 1 to 17.

2. A process according to claim 1, wherein there is administered a said complex wherein the paramagnetic metal is selected from the group consisting of iron, manganese, copper, cobalt, chromium and nickel.

3. A process according to claim 1, wherein there is administered a said complex wherein the paramagnetic metal is iron.

4. A process according to claim 1, wherein there is administered a said complex wherein the paramagnetic metal is selected from the group consisting of gadolinium, lanthanum, cerium, praseodymium, neodymium, promethium, samarium, europium, terbium, dysprosium, holmium, erbium, thulium, ytterbium and lutetium.

5. A process according to claim 1, wherein there is administered a said complex wherein the paramagnetic metal is gadolinium.

6. A process according to claim 1, wherein said complex is administered orally or parenterally at a dosage of 1 to 100 μmol complex/kg bodyweight.

7. A process according to claim 2 wherein said complex is administered orally or parenterally at a dosage of 1 to 100 μmol complex/kg bodyweight.

8. A process according to claim 3 wherein said complex is administered orally or parenterally at a dosage of 1 to 100 μmol complex/kg bodyweight.

9. A process according to claim 4 wherein said complex is administered orally or parenterally at a dosage of 1 to 100 μmol complex/kg bodyweight.

10. A process according to claim 5 wherein said complex is administered orally or parenterally at a dosage of 1 to 100 μmol complex/kg bodyweight.

11. A process according to claim 1 comprising administering as said complex a complex of a paramagnetic metal and 6-carboxymethyl-3,9-bis(methylcarbamoylmethyl)-3,6,9-triazaundecanedioic acid.

12. A process according to claim 1 comprising administering as said complex a complex of a paramagnetic metal and 6-carboxymethyl-3,9-bis(ethylcarbamoylmethyl)-3,6,9-triazaundecanedioic acid.

13. A process according to claim 1 comprising administering as said complex a complex of a paramagnetic metal and 6-carboxymethyl-3,9-bis(propylcarbamoylmethyl)-3,6,9-triazaundecanedioic acid.

14. A process according to claim 1 comprising administering as said complex a complex of a paramagnetic metal and 6-carboxymethyl-3,9-bis(butylcarbamoylmethyl)-3,6,9-triazaundecanedioic acid.

15. A process according to claim 1 comprising administering as said complex a complex of a paramagnetic metal and 6-carboxymethyl-3,9-bis(pentylcarbamoylmethyl)-3,6,9-triazaundecanedioic acid.

16. A process according to claim 1 comprising administering as said complex a complex of a paramagnetic metal and 6-carboxymethyl-3,9-bis(hexylcarbamoylmethyl)-3,6,9-triazaundecanedioic acid.

17. A process according to claim 1 comprising administering as said complex a complex of a paramagnetic metal and 6-carboxymethyl-j,9-bis(heptylcarbamoylmethyl)-3,6,9-triazaundecanedioic acid.

18. A process according to claim 11 comprising administering as said complex a complex of a paramagnetic metal and 6-carboxymethyl-3,9-bis(octylcarbamoylmethyl)-3,6,9-triazaundecanedioic acid.

19. A process according to claim 1 comprising administering as said complex a complex of a paramagnetic metal and 6-carboxymethyl-3,9-bis(nonylcarbamoylmethyl)-3,6,9-triazaundecanedioic acid.

20. A process according to claim 1 comprising administering as said complex a complex of a paramagnetic metal and 6-carboxymethyl-3,9-bis(decylcarbamoylmethyl)-3,6,9-triazaundecanedioic acid.

21. A process according to claim 1 comprising administering as said complex a complex of a paramagnetic metal and 6-carboxymethyl-3,9-bis(hexadecylcarbamoylmethyl)-3,6,9-triazaundecanedioic acid.

* * * * *